US007462150B1

(12) United States Patent
Bharmi

(10) Patent No.: US 7,462,150 B1
(45) Date of Patent: Dec. 9, 2008

(54) SYSTEM AND METHOD FOR EVALUATING IMPAIRED GLUCOSE TOLERANCE AND DIABETES MELLITUS WITHIN A PATIENT USING AN IMPLANTABLE MEDICAL DEVICE

(75) Inventor: Rupinder Bharmi, Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 425 days.

(21) Appl. No.: 11/450,937

(22) Filed: Jun. 9, 2006

(51) Int. Cl.
*A61B 5/00* (2006.01)
(52) U.S. Cl. ...................................... 600/300; 600/365
(58) Field of Classification Search ................. 600/300, 600/365
See application file for complete search history.

(56) References Cited

U.S. PATENT DOCUMENTS

| | | | |
|---|---|---|---|
| 4,759,366 A | 7/1988 | Callaghan | 128/419 PG |
| 5,476,483 A | 12/1995 | Bornzin et al. | 607/17 |
| 5,741,211 A * | 4/1998 | Renirie et al. | 600/300 |
| 5,844,862 A * | 12/1998 | Cocatre-Zilgien | 368/10 |
| 6,449,509 B1 | 9/2002 | Park et al. | 607/20 |
| 6,645,153 B2 | 11/2003 | Kroll et al. | 600/481 |
| 6,658,292 B2 | 12/2003 | Kroll et al. | 607/19 |
| 2004/0077962 A1 | 4/2004 | Kroll | 600/513 |
| 2004/0078065 A1* | 4/2004 | Kroll | 607/60 |
| 2006/0167365 A1* | 7/2006 | Bharmi | 600/517 |
| 2006/0241510 A1* | 10/2006 | Halperin et al. | 600/534 |

FOREIGN PATENT DOCUMENTS

WO   WO 2005/028029 A2   3/2005
WO   WO 2005/028029 A3   3/2005

OTHER PUBLICATIONS

Mander, Bryce et al., "*Short Sleep: A Risk Factor for Insulin Resistance and Obesity,*" Diabetes. 2001;50:Abstract 183-OR.
Meslier, N. et al., "*Impaired glucose-insulin metabolism in males with obstructive sleep apnoea syndrome,*" Eur Respir J 2003; 22:156-160.
Redmond, Stephen J. et al., "*Cardiorespiratory-Based Sleep Staging in Subjects with Obstructive Sleep Apnea,*" IEEE Trans Biomed Eng Mar. 2006; 53(3):485-96.
Spiegel, Karine et al., "*Impact of sleep debt on metabolic and endocrine function,*" The Lancet. 1999;354:1435-1439.
Gottlieb, Daniel J. MD et al., "Association of Sleep Time With Diabetes Mellitus and Impaired Glucose Tolerance," Arch Intern Med 2005;165-863-868.

* cited by examiner

*Primary Examiner*—Robert L. Nasser, Jr.
*Assistant Examiner*—Karen E Toth

(57) ABSTRACT

Techniques are described for use by a pacemaker or implantable cardioverter/defibrillator (ICD) or other implantable medical device. The techniques are provided for evaluating the likelihood that the patient, in which the device is implanted, has impaired glucose tolerance (IGT) or diabetes mellitus. Briefly, a value representative of sleep quality of the patient is detected and then the likelihood that the patient has IGT or diabetes mellitus is determined based on the sleep quality value. In this regard, it has been found that a decrease in overall sleep quality is associated with an increased likelihood of IGT or diabetes mellitus, which is in turn associated with an increased risk of mortality. Hence, sleep quality may be used as a proxy for evaluating the likelihood that the patient has IGT or diabetes mellitus and for assessing associated mortality risk.

16 Claims, 9 Drawing Sheets

SYSTEM AND METHOD FOR EVALUATING IMPAIRED GLUCOSE TOLERANCE AND DIABETES MELLITUS WITHIN A PATIENT USING AN IMPLANTABLE MEDICAL DEVICE

FIELD OF THE INVENTION

The invention generally relates to implantable medical devices such as pacemakers and implantable cardioverter/defibrillators (ICDs) and, in particular, to techniques for evaluating impaired glucose tolerance, diabetes mellitus and associated mortality risk within a patient using such devices.

BACKGROUND OF THE INVENTION

Diabetes is a medical condition wherein the production and use of insulin is impaired, causing glucose levels to increase in the bloodstream. The most common types of diabetes are Type I (i.e. insulin-dependent diabetes) and Type II diabetes (i.e. non-insulin-dependent diabetes), also called diabetes mellitus. Impaired glucose tolerance (IGT) pertains to a medical condition wherein blood glucose levels that are higher than normal, but generally below the level of diabetes. More specifically, IGT is a combination of impaired secretion of insulin and reduced insulin sensitivity (i.e. insulin resistance). Some patients who develop IGT revert to normal glucose tolerance. Others remain in a chronic state of IGT. However, once IGT has developed, insulin secretion and sensitivity usually continue to decline, resulting in diabetes mellitus.

People with IGT are rarely treated because the condition is rarely diagnosed. Accordingly, it would be desirable to provide improved techniques for early detection of IGT so as to permit prompt treatment and it is to that end that the present invention is generally directed. Many patients susceptible to IGT, particularly the elderly, have pacemakers, ICDs or other implantable medical devices implanted therein, or are candidates for such devices. Briefly, a pacemaker is an implantable device that recognizes various arrhythmias such as an abnormally slow heart rate (i.e. bradycardia) or an abnormally fast heart rate (i.e. tachycardia) and delivers electrical pacing pulses to the heart in an effort to remedy the arrhythmias. An ICD is an implantable device that additionally or alternatively recognizes atrial fibrillation (AF) or ventricular fibrillation (VF) and delivers electrical shocks to terminate such fibrillation. Pacemakers and ICDs detect arrhythmias by sensing internal electrical cardiac signals using leads implanted within the heart. The internal signals comprise an intracardiac electrogram (IEGM). State-of-the-art pacemakers and ICDs are also typically capable of detecting a wide range of other parameters indicative of the physiology of the patient.

As many patients susceptible to IGT already have a pacemaker or ICD implanted therein, or are candidates for such devices, it would be desirable to provide techniques for detecting IGT using a pacemaker or ICD. Detection using a pacemaker or ICD would permit early detection of the condition. In turn, early detection permits early treatment, which improves the overall prognosis for the patient. In particular, early detection and treatment of IGT helps prevent the onset of diabetes mellitus through appropriate diet or therapy. Heretofore, however, the Applicant is unaware of any techniques for use with pacemakers, ICDs or other implantable medical devices that are specifically directed to detecting or evaluating IGT within the patient. Accordingly, certain aspects of the present invention are directed to filling that need. Other aspects of the invention are directed to techniques for detecting or evaluating diabetes mellitus within the patient, should that condition nevertheless arise. Still other aspects are directed to detecting the risk of mortality arising due to IGT or diabetes mellitus within the patient. Herein, IGT and diabetes mellitus are collectively referred to as "abnormal glucose level medical conditions."

SUMMARY OF THE INVENTION

In accordance with the invention, techniques are provided for use with an implantable medical device for evaluating the likelihood that the patient in which the device is implanted has an abnormal glucose level medical condition, such as IGT or diabetes mellitus. Briefly, a value representative of sleep quality of the patient is detected, and then the likelihood that the patient has the abnormal glucose level medical condition is evaluated based on the sleep quality value. In this regard, it has been found that a decrease in overall sleep quality of a patient is associated with an increased likelihood of IGT or diabetes mellitus, which is in turn associated with an increased risk of mortality. Hence, sleep quality may be used as a proxy for evaluating the likelihood that the patient has IGT or diabetes mellitus and for assessing the risk of associated mortality.

In one example, the implantable device detects sleep quality by determining the extent to which a nightly total sleep period (TSP) deviates from a normal sleep range (NSR). A significant and persistent deviation (either longer or shorter) from the normal sleep range is indicative of an increased likelihood of IGT or diabetes mellitus within the patient. In another example, the implantable device detects sleep quality by determining a "sleep efficiency" value (SE) based on various parameters detected using implantable sensors and leads. A significant and persistent reduction in sleep efficiency (SE) is also indicative of an increased likelihood of IGT or diabetes mellitus.

In an exemplary implementation, the implanted device detects sleep efficiency (SE) by detecting the following events and parameters:
  (1) the onset of an extended period of sleep of the patient (SO);
  (2) the final awakening from the period of sleep (FA);
  (3) any temporary awake time during the period of sleep (TAT); and
  (4) the total interval of time the patient spends in the sleep position (TSSP) during the period of sleep; and
  (5) any time spend moving while during the overall period of sleep (TSP) asleep.

Based on these parameters, sleep efficiency (SE) is determined as follows. First, a total sleep period (TSP) is calculated as the total time from onset of sleep (SO) to final awakening (FA). Then, a total quality sleep time (TQST) is calculated as the total sleep period (TSP) less the time spent moving (TSM) and less any temporary awake time (TAT):

$$TQST = TSP - TSM - TAT.$$

Sleep efficiency (SE) is then calculated as the ratio of total quality sleep time (TQST) to time spent in sleep position (TSSP):

$$SE = TQST/TSSP.$$

Preferably, a new sleep efficiency value (SE) is calculated every morning, based on sleep data collected the preceding night. The SE values may be recorded within the implanted device for subsequent physician review or, if the device is in communication with a bedside monitor, the values may be transmitted to the monitor for storage therein or for relaying to the physician. The implantable device may also be configured to compare the latest sleep efficiency (SE) values against a predetermined threshold value indicative of the presence of IGT or diabetes mellitus. In one example, if SE falls below a threshold indicative of the likely onset of IGT or diabetes mellitus, then suitable warning signals are generated and/or diagnostic information is stored for subsequent physician review. Warning signals may be generated, e.g., using an implanted warning device or using the bedside monitor. The SE value may also be compared against various thresholds indicative of various levels of associated mortality risk, with generation of appropriate warning signals and storage of appropriate diagnostic data. Both the NSR deviation evaluation technique and SE evaluation technique may be exploited by the implanted device to thereby provide a more robust evaluation procedure.

In a preferred implementation, wherein the implantable medical device is a pacemaker or ICD, the onset of a period of sleep of the patient (SO) and the final awakening from the period of sleep (FA) are detected by the device based on changes in one or more of (a) heart rate variability, (b) IEGM morphology, (c) respiration rate, (d) respiration depth and (e) blood pressure. Heart rate variability, IEGM morphology, respiration rate, and respiration depth are derived from the IEGM of the patient sensed using implanted sensing/pacing leads. Blood pressure may be detected using an implanted blood pressure sensor or other appropriate detection technique. Any time spend moving (TSM) during the sleep period may be detected, for example, based on changes in one or more of (a) IEGM morphology, (b) a paced depolarization integral (PDI), and (c) patient movement sensed using an implanted activity sensor. Any temporary awake time (TAT) may be detected based on changes in one or more of (a) heart rate variability derived from the IEGM, (b) patient motion sensed using the activity sensor and (c) blood pressure sensed using the blood pressure sensor. The total time of the patient spends in sleep position (TSSP) may be detected based on patient posture sensed using an implanted posture sensor. Hence, each of the various parameters are detectable by the implanted device using implanted sensors or leads, thus permitting the device to evaluate sleep efficiency frequently (e.g. daily) for the purpose of evaluating the likelihood of IGT, diabetes mellitus, and associated mortality.

BRIEF DESCRIPTION OF THE DRAWINGS

Further features and advantages of the invention may be more readily understood by reference to the following description taken in conjunction with the accompanying drawings, in which.

DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Overview of Implantable Medical System

Figure 1:
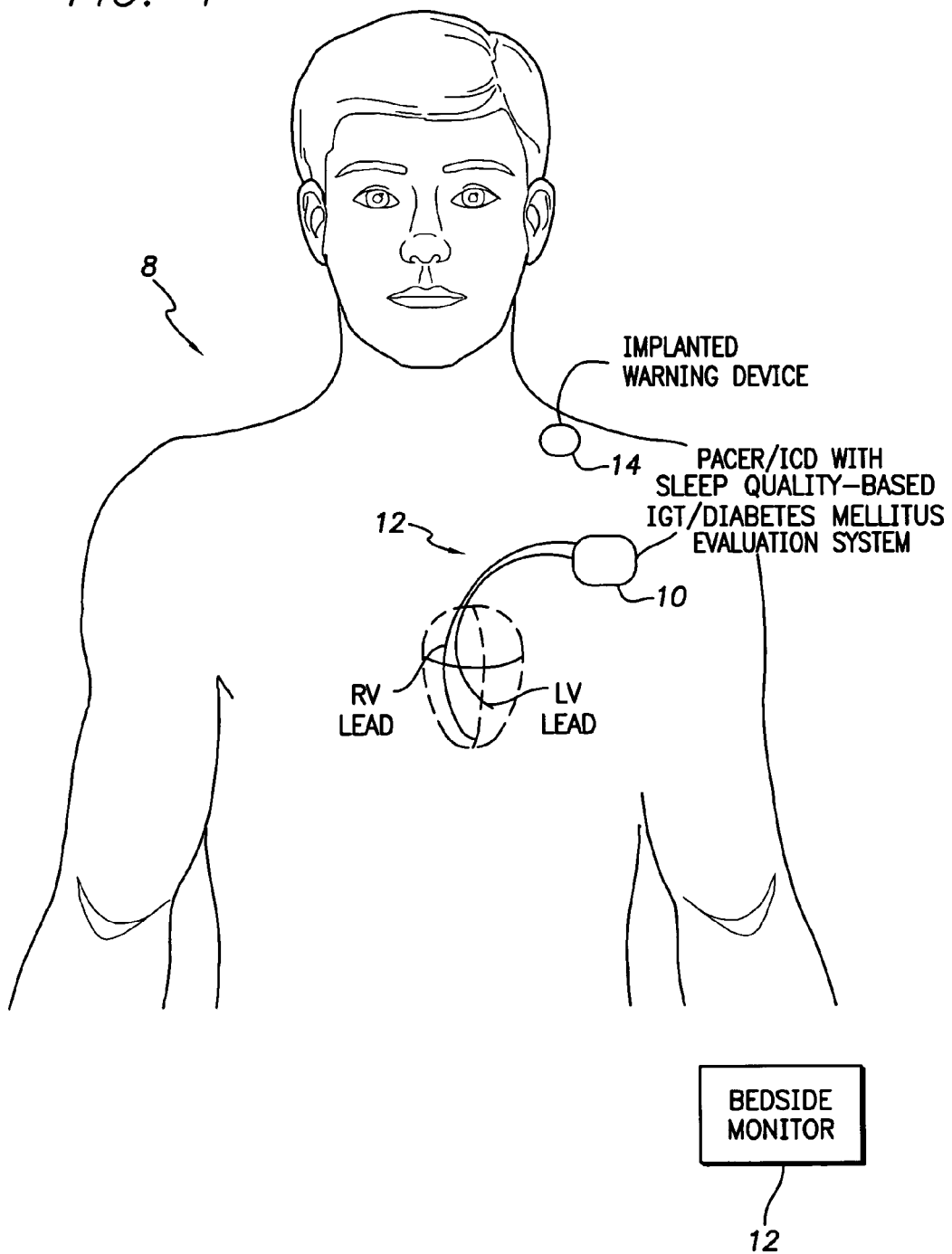
FIG. 1 illustrates pertinent components of an implantable medical system having a pacemaker or ICD equipped to evaluate the likelihood that the patient has IGT or diabetes mellitus based on sleep efficiency (SE)
Figure 8:
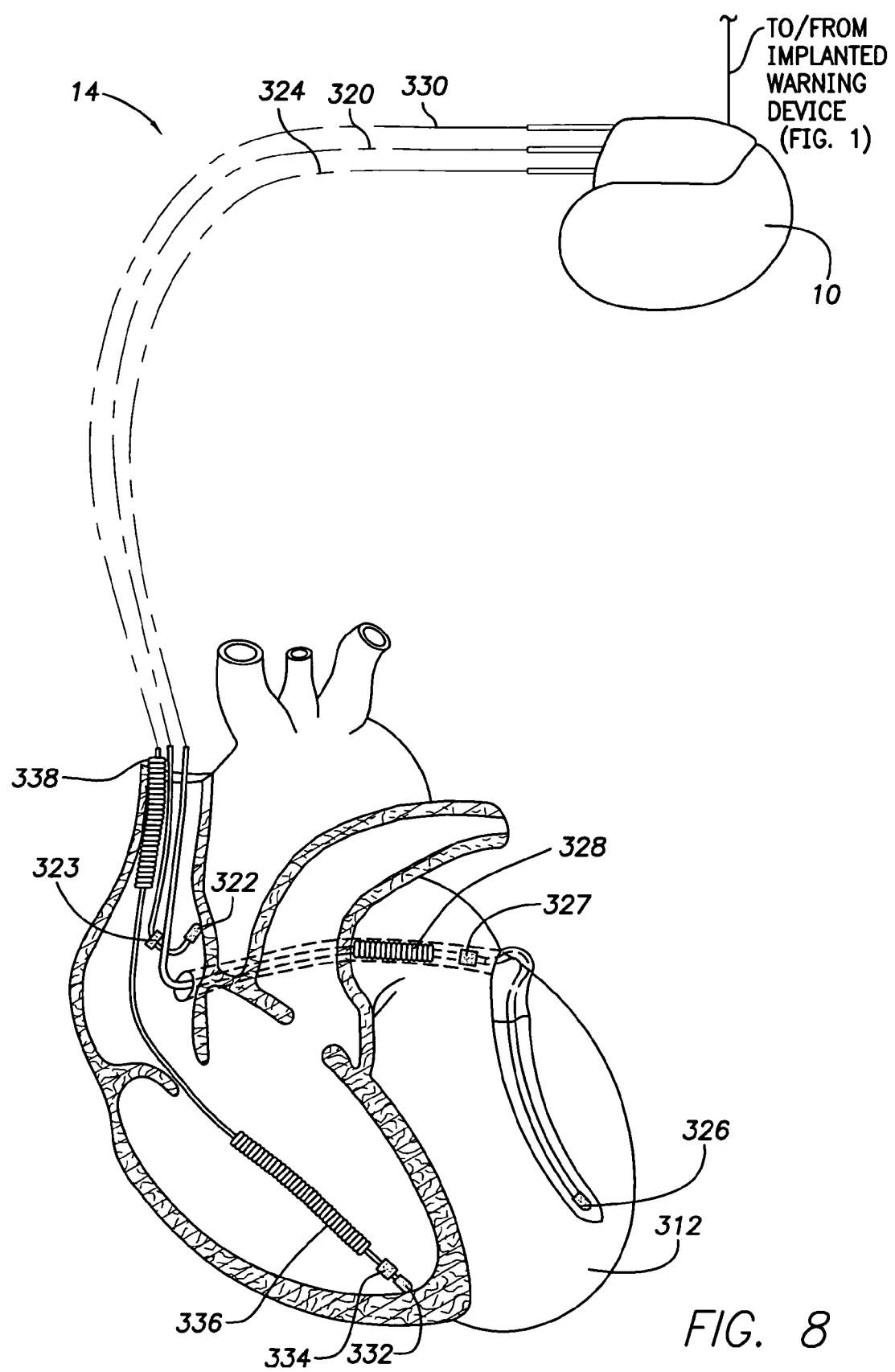
FIG. 8 is a simplified, partly cutaway view, illustrating the pacer/ICD of FIG. 1 along with a set of exemplary leads implanted in the heart of the patient.

FIG. 1 illustrates an implantable medical system 8 having a pacer/ICD 10 equipped to evaluate the likelihood that the patient has IGT or diabetes mellitus based on sleep quality of the patient. Briefly, overall sleep quality of the patient is automatically detected by the pacers/ICD based on an analysis of electrical signals received from pacing leads 12 and from various sensors and detectors to be described below. (In FIG. 1, only two exemplary leads are shown; a complete set of leads is shown in FIG. 8 and described below.) Poor sleep quality is correlated with an increased likelihood of the presence of IGT and diabetes mellitus. As will be explained below, sleep quality can pertain to either the nightly total sleep period (TSP) or the nightly sleep efficiency (SE) of the patient. In any case, sleep quality information obtained by the pacer/ICD is analyzed to detect any sustained decrease in sleep quality that may indicate an increased likelihood of IGT or diabetes mellitus within the patient.

Appropriate diagnostic data pertaining to sleep quality is stored in the pacer/ICD for subsequent physician review and warning signals are automatically generated, if warranted, upon detection of persistent, poor sleep quality. Such warning signals may be delivered directly to the patient using an implanted warning device 14, if one is provided. The implanted warning device may be, for example, a "tickle" warning device that generates a perceptible voltage signal to alert the patent of the need to consult a physician. Alternatively, warning signals may be transmitted by the pacer/ICD to a bedside monitor 16 for display. The bedside monitor may also relay the warning signals to the patient's physician or other appropriate medical personnel. The physician then conducts otherwise routine tests to determine whether the patient indeed has IGT or diabetes mellitus and, if so, the physician then initiates a regime of appropriate therapy. In this manner, early detection of IGT or diabetes mellitus may be achieved via analysis of sleep quality within the patient. As the presence of IGT or diabetes mellitus within a patient affects mortality, the sleep quality diagnostics information generated by the pacer/ICD is also useful to the physician in evaluating the risk of mortality for the particular patient.

Thus, FIG. 1 provides an overview of the implantable medical system for detecting an increased likelihood of IGT or diabetes mellitus with a patient and for assessing associated mortality risk. Although a pacer/ICD is illustrated in FIG. 1, it should be understood that the detection techniques of the invention may be implemented within other implantable devices. Note also that internal signal transmission lines for interconnecting the various implanted components are not shown. Alternatively, wireless signal transmission may be employed. In addition, the particular size, shapes and implant locations of the various components are merely illustrative and do not necessarily correspond to the actual sizes, shapes and locations. In addition, it should be appreciated that systems provided in accordance with invention need not include all of the components shown in FIG. 1. In many cases, for example, the implantable system will include only the pacer/ICD and its leads with no implantable warning device. No attempt is made herein to describe all possible combinations of components that may be provided in accordance with the general principles of the invention.

IGT/Diabetes Mellitus Evaluation Techniques

Figure 2:
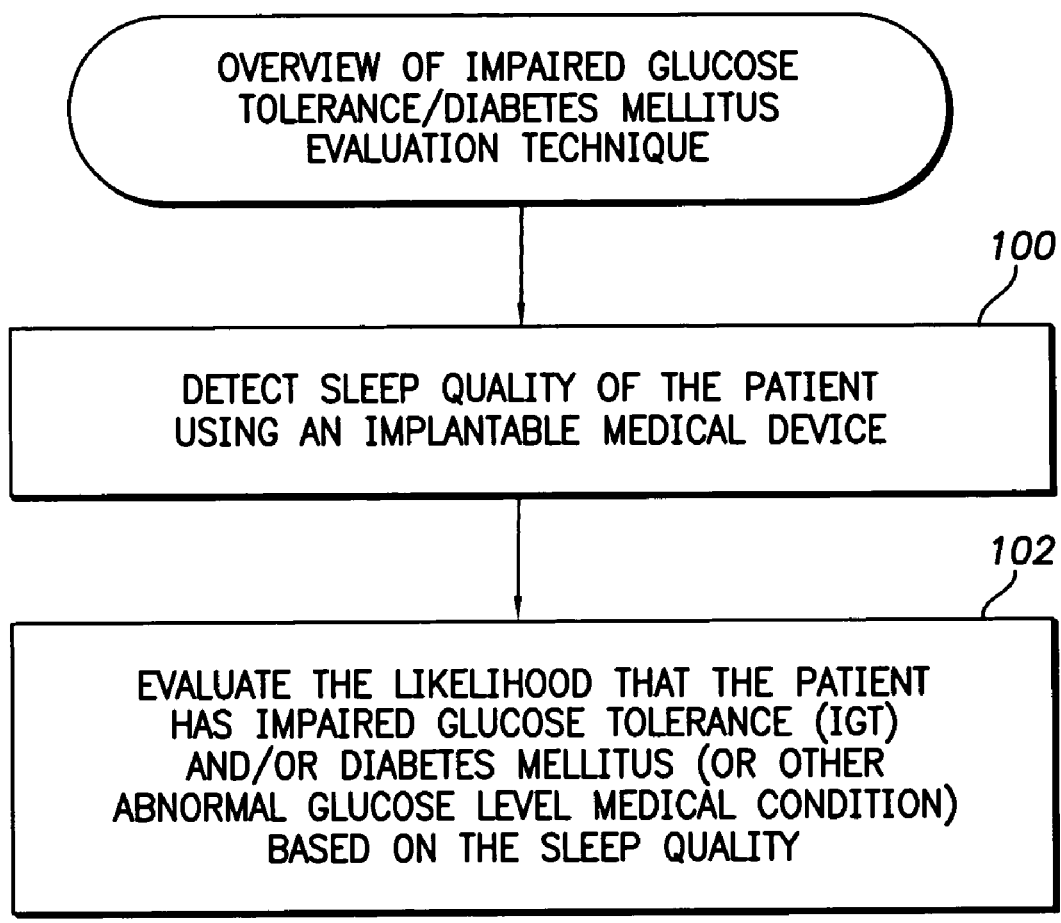
FIG. 2 is a flow chart providing an overview of the evaluation technique employed by the implantable system of FIG. 1.

FIG. 2 summarizes the operations of pacer/ICD 10 of FIG. 1 to detect evaluate IGT/diabetes mellitus. Briefly, at step 100, the sleep quality of the patient is detected by pacer/ICD then, at step 102, the pacer/ICD evaluates the likelihood that the patient has IGT or diabetes mellitus (or other abnormal glucose level medical conditions) based on the detected sleep quality. In this regard, it has been found that experimental restriction of sleep to four hours per night for six nights resulted in temporary IGT in healthy adults, which resolved after one week of increased sleep duration. (See, Spiegel et al., "Impact of sleep debt on metabolic and endocrine function." Lancet. 1999; 354:1435-1439.) The biological mechanisms underlying this effect are uncertain. However, sleep deprivation may lead to increased sympathetic nervous system activity, which may impair glucose regulation via the lipolytic effects of Beta-adrenergic stimulation of visceral adipose tissue. Sleep deprivation also alters activity of the hypothalamic-pituitary-adrenal axis, with short-term partial sleep deprivation causing a shorter quiescent period of cortisol secretion and slower clearance of free cortisol. Experimentally delaying sleep onset is associated with a pre-sleep burst of growth hormone secretion followed by the usual sleep-onset growth hormone secretion, possibly causing morning glucose intolerance. In any case, there is at least a correlation between reduced sleep time and IGT in healthy patients, which suggests that reduced sleep times within a pacer/ICD patient may be indicative of an increased likelihood that the patient has IGT, sufficient to warrant physician review. Since IGT often leads to diabetes mellitus, a persistent reduction in sleep time may also be indicative of an increased likelihood the patient has diabetes mellitus or is at risk of diabetes mellitus. Hence, the pacer/ICD is equipped to track sleep time and to detect a persistent reduction to abnormally low sleep times that might be indicative of IGT or diabetes mellitus and to generate appropriate warning signals.

Moreover, a study by Mander et al. using an intravenous glucose tolerance test in a small sample of healthy, non-obese, young adults with habitual short sleep times (mean, 5.3 hours per night) found that, compared with subjects sleeping 7.5 to 8.5 hours per night, short sleepers were not necessarily glucose intolerant but did have reduced insulin sensitivity. (Mander et al. "Short sleep: a risk factor for insulin resistance and obesity," Diabetes. 2001; 50:Abstract 183-OR.) With additional risk factors, such as advancing age or greater adiposity, reduced insulin sensitivity might result in glucose intolerance. Hence, Mander et al. further supports the conclusion that a reduction in sleep time is correlated with an increased likelihood of IGT and diabetes mellitus, particularly within elderly patients more likely to have pacer/ICDs. Furthermore, Gottlieb et al. have reported that, compared with sleep times of seven to eight hours per night, self reported usual sleep times of six or less, or nine or more, hours per night were associated with a higher adjusted odds ratio for IGT and diabetes mellitus. (Gottlieb et al., "Association of Sleep Time with Diabetes Mellitus and Impaired Glucose Tolerance," Arch Intern Med/Vol 165, Apr. 25, 2005.) Secondary analyses also indicated that the association of sleep time with diabetes mellitus and IGT was not confounded by caffeine or alcohol consumption, cigarette smoking, or use of antihypertensive medications, which might influence sleep habits, or nocturia or prevalent medical illnesses often associated with diabetes mellitus, including hypertension and cardiovascular disease. Hence, the Gottlieb et al. article further supports the conclusion that reduced sleep time is correlated with an increased likelihood of IGT and diabetes mellitus.

Moreover, Gottlieb et al. suggests that abnormally long sleep times are also correlated with both IGT and diabetes mellitus. The mechanisms mediating the association of long sleep time with impaired glucose regulation are speculative, but it is believed in the literature that sleeping for greater than nine hours or more per night leads to impaired glucose regulation though direct effects of inactivity or through an association of inactivity with a greater degree of visceral adiposity for a given level of total body adiposity, as suggested by the greater reduction in visceral compared with total body fat with daily walking. In any case, there is a correlation between abnormally long sleep times and IGT and diabetes mellitus sufficient to warrant physician review. Hence, the pacer/ICD is preferably also equipped to detect any persistent increase to abnormally long sleep times that might be indicative of IGT or diabetes mellitus and to generate appropriate warning signals.

Hence, poor sleep quality, as indicated by either abnormally long or abnormally short sleep times, suggests an increased likelihood of IGT or diabetes mellitus. Poor sleep quality can also occur even if the overall sleep time is otherwise normal. Hence, the pacer/ICD also determines the sleep efficiency (SE) value as an alternate indication of sleep quality. An abnormally low sleep efficiency value is deemed to be indicative of an increased likelihood of IGT or diabetes mellitus. If the device is equipped to also utilize other techniques to detect diabetes mellitus, the sleep quality information obtained by the pacer/ICD may be used on verify or confirm such a determination. Diabetes may potentially be detected, e.g., using blood glucose monitoring techniques described in U.S. Patent Application 2004/0077962, of Kroll, filed Apr. 22, 2004, entitled "System and Method for Monitoring Blood Glucose Levels Using an Implantable Medical Device." Furthermore, as diabetes mellitus carries a high risk of cardiovascular-related mortality, poor sleep quality might increase mortality. Thus, whenever persistent, poor sleep quality is detected by pacer/ICD, appropriate diagnostic data is generated for physician review indicative of a possible increase in risk or mortality within the patient. If the device is equipped to utilize other techniques to evaluate risk of mortality, the sleep quality information obtained by the pacer/ICD may be used in conjunction with such an evaluation. Risk or mortality may be evaluated, e.g., using techniques described in U.S. Pat. No. 6,645,153, to Kroll et al., entitled "System and Method for Evaluating Risk of Mortality Due To Congestive Heart Failure Using Physiologic Sensors."

Figure 3:
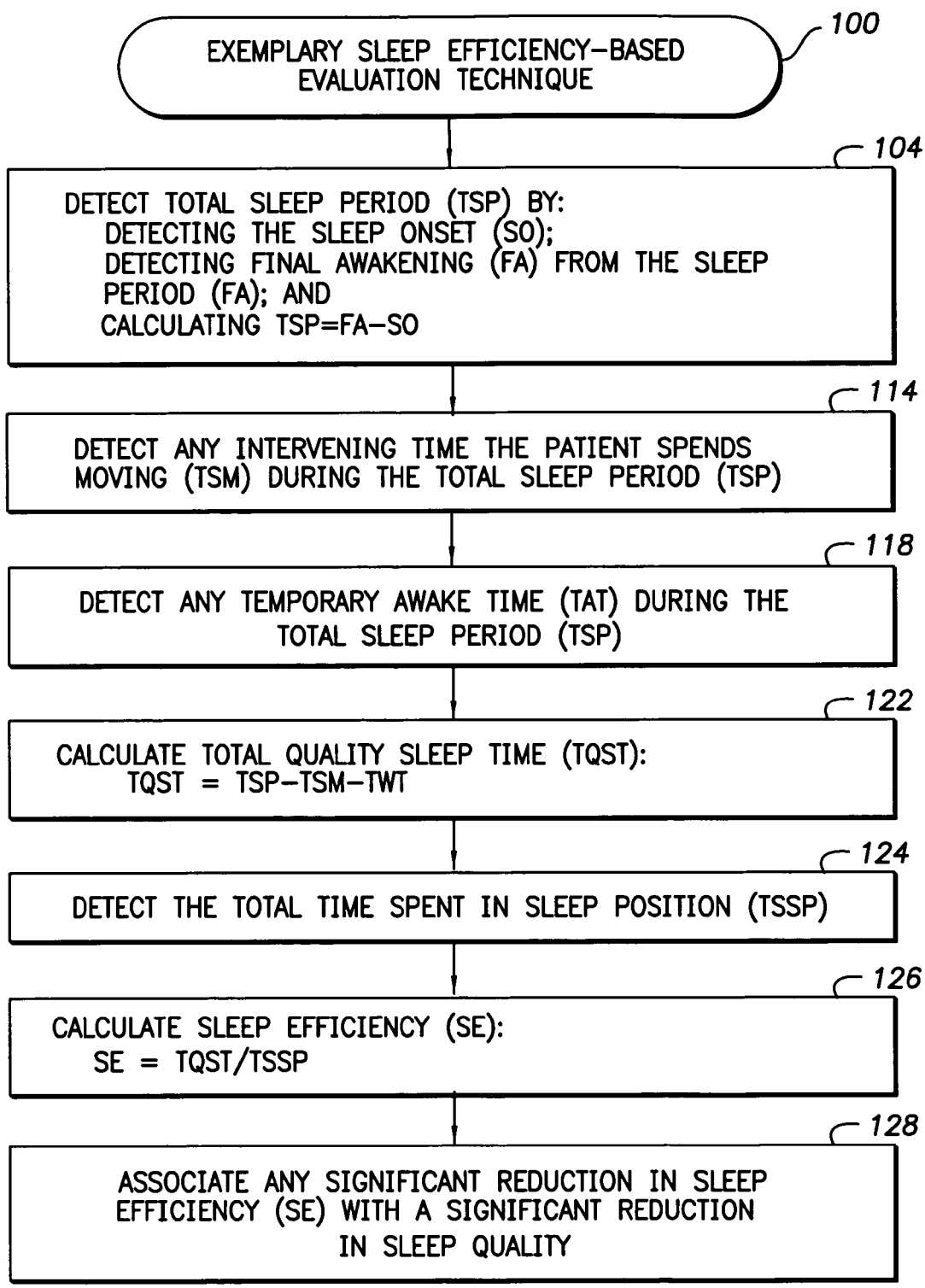
FIG. 3 is a flow chart illustrating an exemplary sleep quality evaluation technique for use with the general technique of FIG. 2, wherein sleep efficiency (SE) is determined.
Figure 4:
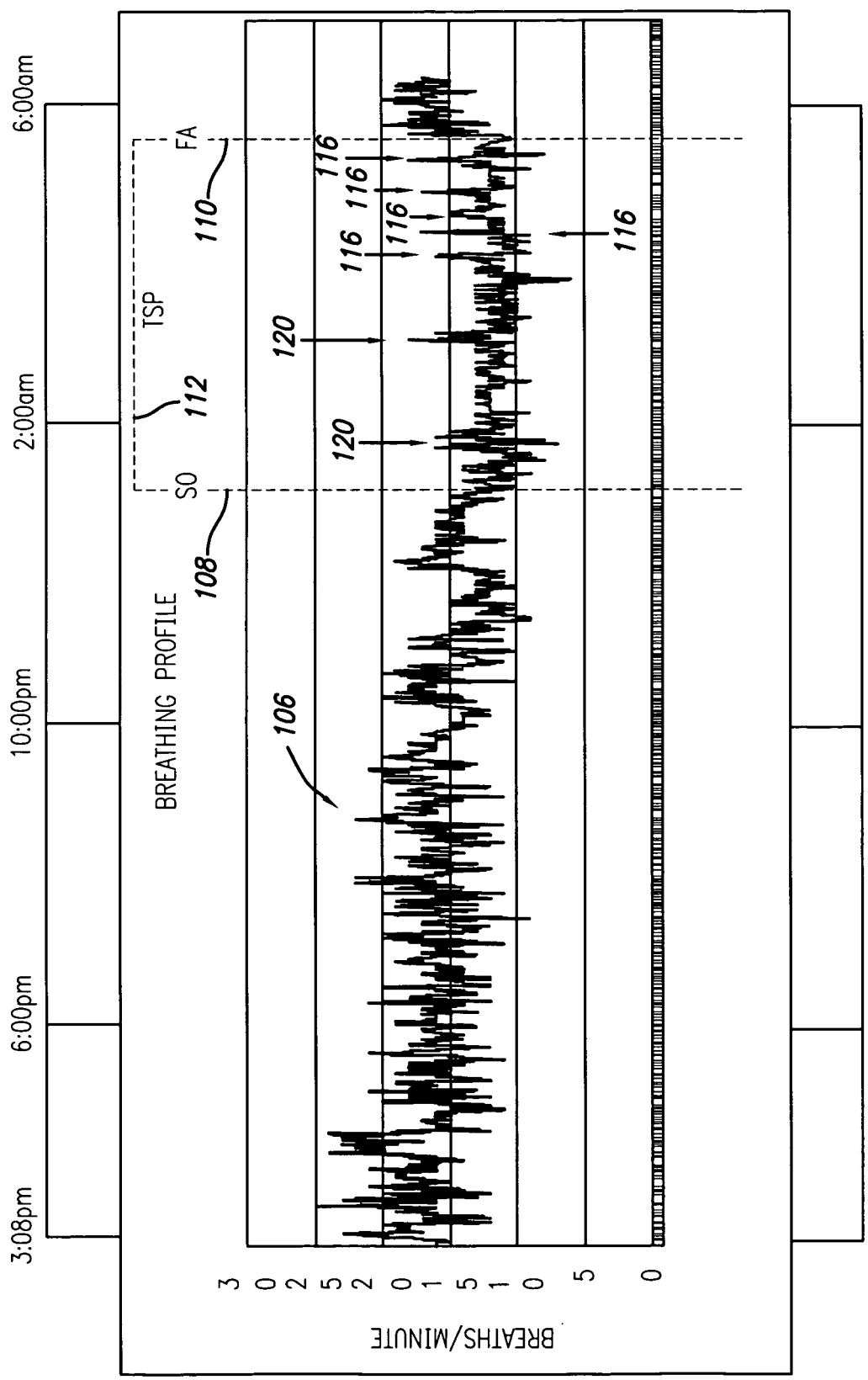
FIG. 4 is a graph illustrating an exemplary respiration profile for a patient and particularly illustrating various sleep interval parameters that may be detected and analyzed using the technique of FIG. 3 to determine sleep efficiency (SE)

Turning now to FIGS. 3 and 4, an exemplary technique for detecting sleep quality based on sleep efficiency will now be described. Beginning at step 104 of FIG. 3, the pacer/ICD detects a nightly total sleep period (TSP) by: detecting the sleep onset (SO); detecting final awakening (FA) from the sleep period; and then calculating TSP=FA−SO. Typically, sleep onset (SO) occurs during the evening with final awakening (FA) occurring the following morning. The time of day as tracked by the pacer/ICD may be used to distinguish the true SO and the true FA of the TSP from the onset of, and awakening from, temporary periods of sleep during the day, such as naps. For a healthy patient, total sleep period (TSP) is typically in the range 7.5 to 8.5 hours per night. Any TSP that is extremely different, such as a TSP of only one hour, is preferably ignored as not being indicative of the true nightly TSP of the patient. Also, note that SO and FA need not be identified immediately as they occur (i.e. in real time) but can instead be identified the following day based on an analysis of recorded sleep parameters. In this regard, there may be a number of false "final" awakenings early in the morning before the true final awakening.

Sleep onset (SO) and final awakening (FA) may be detected based on, e.g., changes in one or more of (a) heart rate variability, (b) IEGM morphology, (c) respiration rate, (d) respiration depth and (e) blood pressure. Heart rate variability, IEGM morphology, respiration rate, and respiration depth may be derived by analyzing the IEGM of the patient sensed by the implanted sensing/pacing leads using otherwise conventional techniques. In this regard, heart rate variability, respiration rate and respiration depth usually decrease upon sleep onset and then increase again upon final awakening. FIG. 4 illustrates an exemplary respiration rate profile 106 showing sleep onset (SO) 108 and final awakening (FA) 110 of a single total sleep period (TSP) 112. Similar profiles may be obtained by the pacer/ICD for respiration depth and heart rate variability.

Respiration rate or depth may also be derived via an analysis of thoracic impedance as described in U.S. Pat. No. 6,449,509 to Park, et al., "Implantable Stimulation Device Having Synchronous Sampling for a Respiration Sensor." See, also, U.S. patent application Ser. No. 11/127,389, filed May 11, 2005 of Bharmi et al., entitled "System and Method for Detection of Respiration Patterns via Intracardiac Electrogram Signals." Blood pressure may be detected using an implanted blood pressure sensor or other appropriate detection technique. See, for example, U.S. patent application Ser. No. 11/378,604, of Kroll et al., filed Mar. 16, 2006, and entitled "System and Method for Detecting Arterial Blood Pressure Based on Aortic Electrical Resistance Using an Implantable Medical Device." Heart rate variability is discussed in U.S. Pat. No. 5,476,483, to Bornzin et al., entitled "System and Method for Modulating the Base Rate during Sleep for a Rate-responsive Cardiac Pacemaker." Insofar as IEGM morphology is concerned, techniques for detecting sleep based changes to the IEGM are described in U.S. patent application Ser. No. 11/416,317, of Bharmi-Sarai et al., filed May 1, 2006, entitled "System and Method for Detecting Abnormal Respiration via Respiratory Parameters Derived from Intracardiac Electrogram Signals", which is incorporated by reference herein. Note also that sleep state (as compared to awake state) is accompanied by a decrease in breathing depth, a decrease in breathing rate (see FIG. 4), and a decrease in heart rate, all of which affect the morphology of the IEGM. Also, during REM sleep and arousals from sleep, the heart rate and breathing rate are irregular. For example, Redmond et al. have described attempts to discern certain sleep stages based, in part, on R-R intervals and achieved an accuracy of 79%. See, Redmond et al., "Cardiorespiratory-Based Sleep Staging in Subjects with Obstructive Sleep Apnea," IEEE Trans Biomed Eng 2006 March; 53(3):485-96.

Next, at step 114 of FIG. 3, the pacer/ICD detects and accumulates (i.e. sums) any intervening time intervals during the total sleep period that the patient spends moving (TSM) while still asleep. FIG. 4 identifies a few exemplary periods of time 116 wherein the patient moves while still asleep. TSM represents the sum of these time intervals of which there may be many during a single TSP. The time spend moving (TSM) during the sleep period may be detected, for example, based on changes in one or more of (a) IEGM morphology, (b) a paced depolarization integral (PDI), and (c) patient movement sensed using an implanted activity sensor. (For a description of PDI, also known as the ventricular depolarization gradient, see U.S. Pat. No. 4,759,366, to Callaghan.) The use of an activity sensor is preferred as it provides a particularly reliable and straightforward indication of patient movement. Changes in IEGM morphology and the PDI also provide an indication of patient movement. In this regard, patient movement usually is accompanied by changes in heart rate and respiration, which in turn affect IEGM morphology and PDI. Again, see the patent application of Bharmi-Sarai et al. cited above. As can be appreciated, some minimal threshold of movement is employed so as to exclude slight movement due to respiration. TSM intervals need not be identified immediately upon their occurrence but may be identified the following day based on an analysis of stored sleep parameters.

At step 118 of FIG. 3, the pacer/ICD detects and measures any intervening time during the overall total sleep period (TSP) that the patient is temporarily awake, i.e. temporary awake time (TAT). Any temporary awake time (TAT) may be detected based on changes in one or more of (a) heart rate variability derived from the IEGM, (b) patient motion sensed using the activity sensor and (c) blood pressure sensed using the blood pressure sensor. FIG. 4 identifies exemplary periods of time 120 wherein the patient is temporarily awake. Note that the pacer/ICD need not actually distinguish temporary awake time (TAT) from time spent moving while asleep (TSM) since it is actually the sum total of these intervals that is of interest. In other words, it is sufficient for the pacer/ICD to merely track the total time spent either moving or temporarily awake within the total sleep period (TSP). As with the other intervals, TAT intervals need not be identified in real time but may be identified the following day by examining stored sleep parameters.

At step 122 of FIG. 3, the pacer/ICD then calculates the total quality sleep time (TQST) as:

$$TQST = TSP - TSM - TAT.$$

Hence, TQST represents the total accumulated time from sleep onset (SO) to final awakening (FA) wherein the patient is actually asleep and not moving significantly. TQST excludes any temporary waking time and also excludes any time spend asleep but moving. That is, the TQST excludes any time intervals wherein the patient is not receiving quality sleep.

At step 124, the pacer/ICD detects the total time spent in the sleep position (TSSP) in connection with a TSP. That is, the pacer/ICD detects and accumulates any intervals of time spend lying down. TSSP may be detected based on patient posture sensed using an implanted posture sensor or other suitable technique. See, e.g., techniques described in U.S. Pat. No. 6,658,292 of Kroll et al., entitled "Detection of patient's position and activity status using 3D accelerometer-based position sensor." See, also, U.S. patent application Ser. No. 10/329,233, of Koh et al., entitled "System and Method for Determining Patient Posture Based On 3-D Trajectory Using an Implantable Medical Device," filed Dec. 23, 2002. Note that TSSP intervals typically begin before sleep onset (SO) and do not end until sometime after the final awakening (FA). Hence, TSSP intervals are not limited to occurring during the total sleep period (TSP). In one example, after the pacer/ICD identifies the SO and FA times, the pacer/ICD then identifies any TSSP intervals immediately prior to SO and immediately subsequent to FA. These may be identified by noting any substantially continuous intervals in the sleep position prior to SO and after FA. These intervals are added to all detected intervals in the sleep position occurring between SO and FA, i.e. during the TSP. Typically, almost all of the time during the TSP is spent in the sleep position. However, the patient may temporarily sit up or stand up at various times during the night, perhaps to go to the toilet, and any such intervals of time would be excluded from TSSP.

Next, at step 126, the pacer/ICD calculates a sleep efficiency (SE) value as the ratio of the total quality sleep time (TQST) to the time spent in sleep position (TSSP), i.e. the pacer/ICD calculates:

$$SE = TQST/TSSP.$$

Ideally, most of the time spent in the sleep position is quality sleep and hence SE is preferably near 1.0. However, even for healthy patients, some amount of time spent in the sleep position is spent wake and/or moving. Thus, even for healthy patients, SE may be less than 1.0. For patients with IGT or diabetes mellitus, however, SE is often considerably less than 1.0 for the reasons already described in connection with FIG. 2. Preferably, the pacer/ICD detects a new value for SE each morning based on the preceding night's sleep and stores the value for trend analysis. Any persistent and significant reduction in SE over time is associated with a significant reduction in sleep quality, at step 128, which is in turn associated with an increase likelihood of IGT, diabetes mellitus and associated mortality (step 102 of FIG. 2.)

Figure 5:
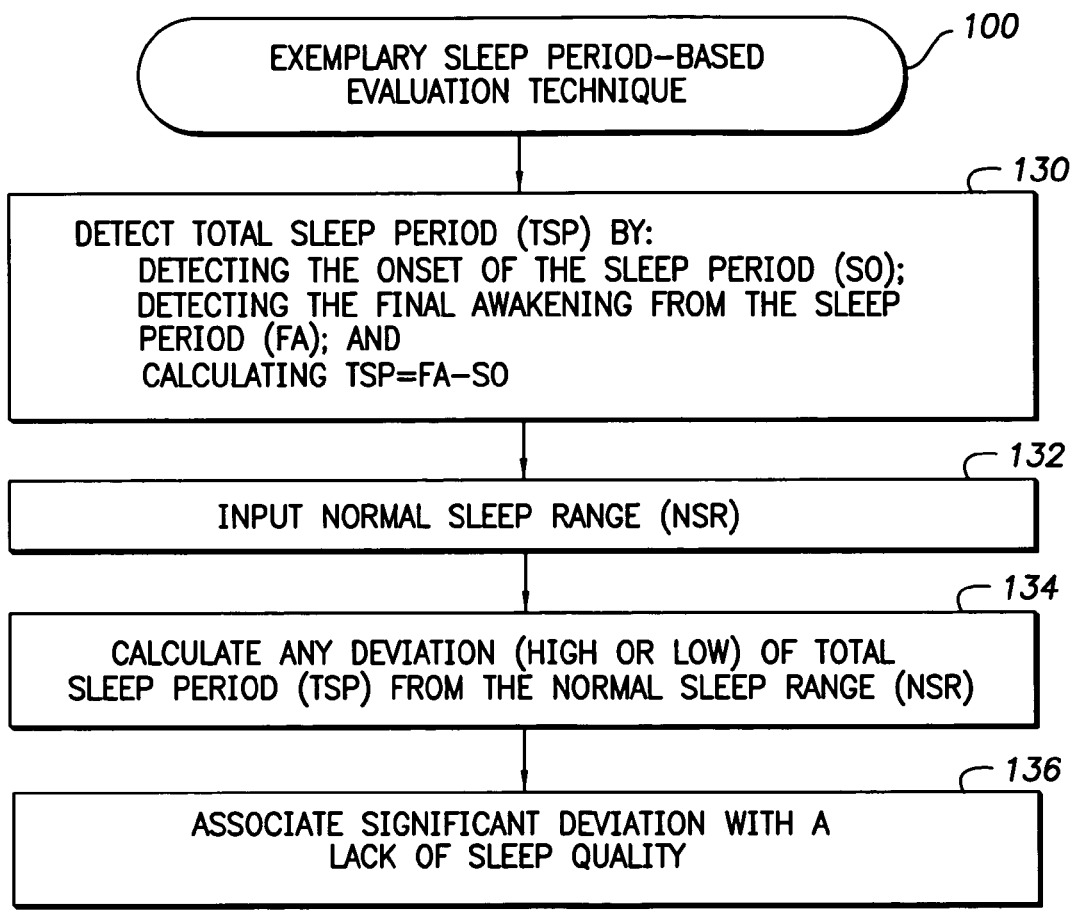
FIG. 5 is a flow chart illustrating another exemplary sleep quality evaluation technique for use with the general technique of FIG. 2, wherein a deviation from a normal sleep range or duration is determined.

Turning now to FIG. 5, an alternate sleep quality evaluation technique is summarized, which only examines the total sleep period (TSP) rather than sleep efficiency (SE). At step 130, the pacer/ICD detects the total sleep period (TSP), which may be accomplished as described above in connection with step 104 of FIG. 3. Next, at step 132, the pacer/ICD inputs a normal sleep range (NSR), which a predetermined range of values corresponding to the normal total sleep period (TSP) for a healthy patient. This may be set, e.g., to a default 7.5 to 8.5 hours. Alternatively, if the patient is initially know to not have IGT or diabetes mellitus, the pacer/ICD may calculate a baseline NSR for the particular patient based on actual sleep habits, so that subsequent changes from that baseline can be detected. In any case, at step 134, the pacer/ICD calculates the amount of deviation of TSP from NSR, if any. For example, if NSR is set to 7.5-8.5 hours, and the patient is slept 9.0 hours, the amount of the deviation is thereby 0.5 hours. Any persistent and significant deviation in TSP from the NSR is deemed indicative of a lack of sleep quality for the reasons already described in connection with FIG. 2. That is, a sleep period that is either too long or too short is deemed to be a poor quality sleep period. Hence, at step 136, any persistent and significant deviation in TSP from NSR over time is associated with a significant reduction in sleep quality, which is in turn associated with an increase likelihood of IGT, diabetes mellitus and associated mortality (step 102 of FIG. 2.)

Hence, FIGS. 3 and 5 set forth alternate techniques for evaluating sleep quality within a patient using a pacer/ICD. In some embodiments, both the SE-based sleep quality evaluation of FIG. 3 and the TSP deviation-based sleep quality evaluation of FIG. 5 are implemented to provide a more robust evaluation of sleep quality. In other embodiments, alternate techniques may instead be employed that do not necessarily rely on either sleep efficiency (SE) or total sleep time (TST). See, e.g., techniques described in WO 2005/028029 of Stahmann et al., entitled "Patient Monitoring, Diagnosis, and/or Therapy Systems and Methods." In general, any suitable of technique for reliably evaluating the sleep quality of a patient may be used, so long as the resulting sleep quality value is adequately correlated with IGT and/or diabetes mellitus or other abnormal blood glucose medical conditions. Note that, although the evaluation techniques are preferably performed by the pacer/ICD itself, the evaluation techniques may alternatively be performed by an external device (such as a bedside monitor) based on sleep data transmitted from the pacer/ICD to the bedside monitor or based on sleep data collected by external sensors.

Figure 6:
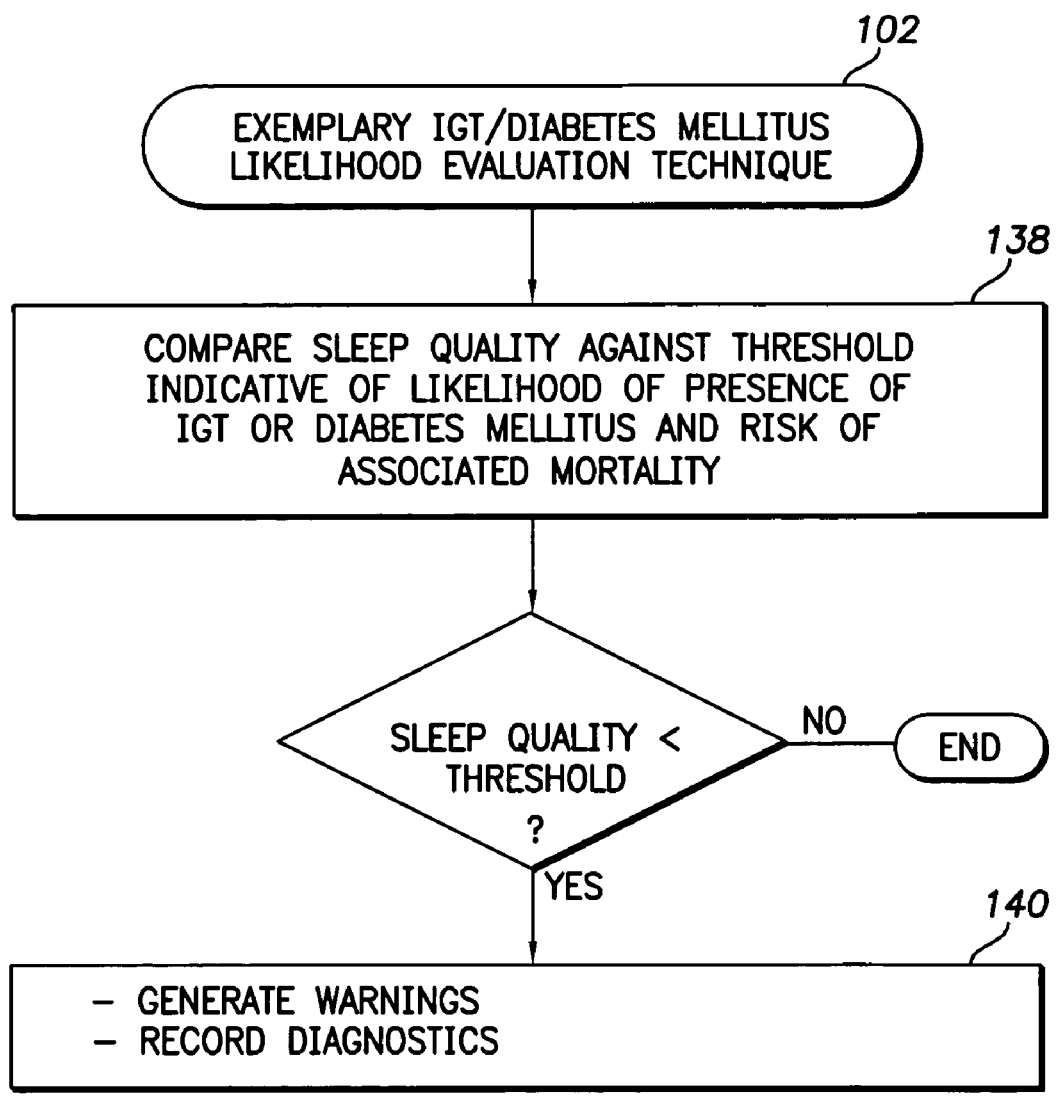
FIG. 6 is a flow chart illustrating an exemplary threshold-based IGT/diabetes mellitus evaluation technique for use with the general technique of FIG. 2.

Once sleep quality has been evaluated, the likelihood of IGT and diabetes mellitus and the associated mortality risk may be evaluated using, e.g., the exemplary technique of FIG. 6. Beginning at step 138, the pacer/ICD compares the current sleep quality of the patient against a threshold indicative of an elevated likelihood of IGT or diabetes mellitus within the patient. In one example, the pacer/ICD calculates an average of recent sleep quality values for comparison against a predetermined threshold. If the average falls below the threshold, then at step 140 appropriate warning signals are generated indicating an elevated likelihood of IGT or diabetes mellitus and an elevated risk of associated mortality. As explained above, the warnings are relayed to the patient and/or physician. Also at step 140, diagnostic data is recorded for physician review, which may include a record of specific sleep quality values that the physician can then examine. In one particular example, the pacer/ICD initially calculates a baseline sleep quality for the patient following device implant (after the patient has recovered from the implant procedure) and then detects any significant reduction in sleep quality from the baseline. Hence, in that example, it is not the absolute sleep quality that matters, but the deviation from the patient's own baseline.

Figure 7:
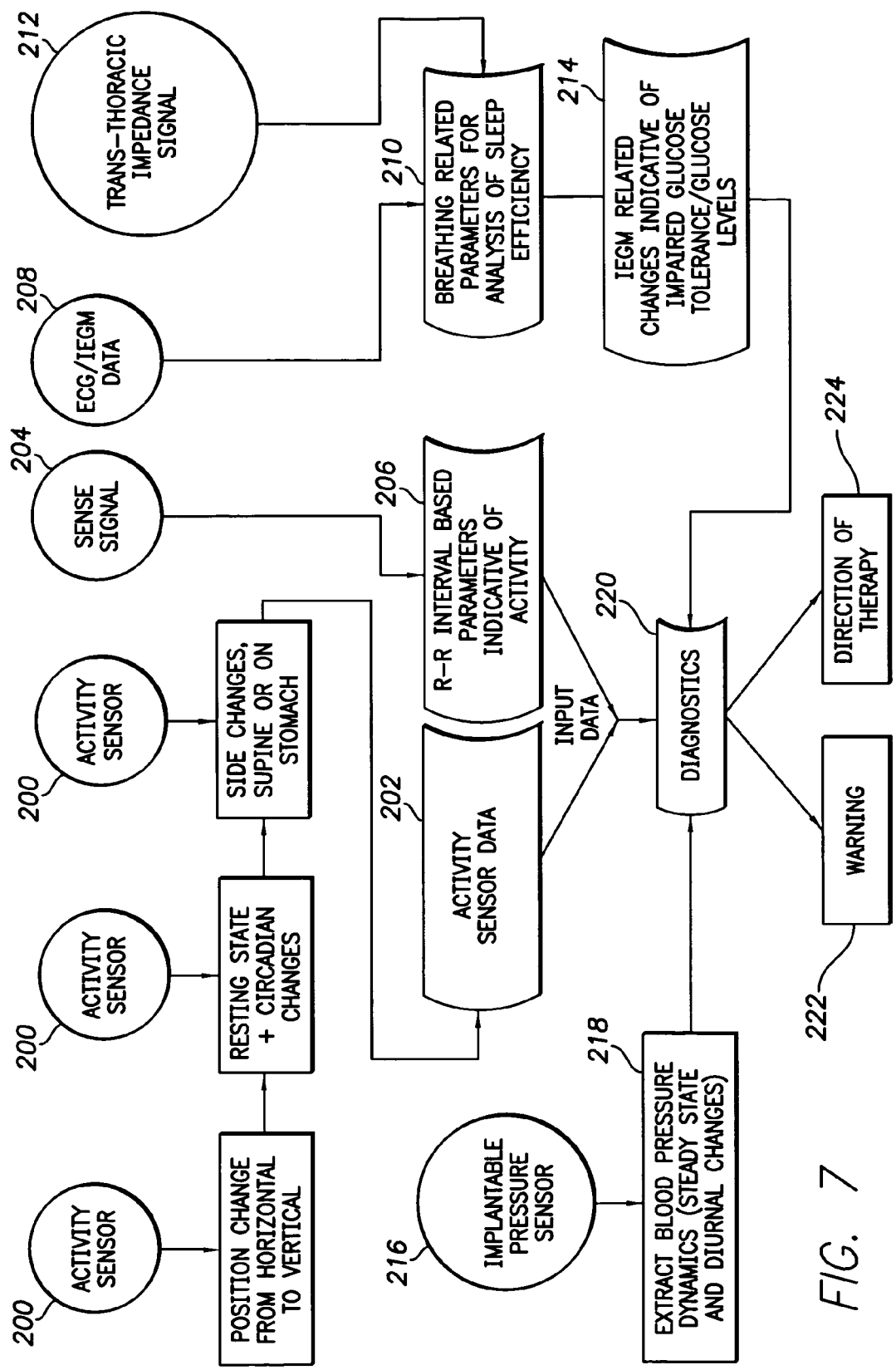
FIG. 7 is a flow chart illustrating the use of data from various sensors in connection with the technique of FIG. 2.

FIG. 7 summarizes the various sensors that may be used in connection with the techniques of FIGS. 2-6 along with the various types of information obtained and analyzed. One or more activity sensors 200 are used to detect vertical changes in posture (e.g. changes from horizontal to vertical or vice versa), changes in the resting state or circadian state of patient, and horizontal changes in posture (e.g. changes from a supine to a prone position or vice versa). Information from the activity sensors is collectively referred to as activity sensor data 202. A sense signal 206 received from pacing/sensing leads is used to derive R-R interval parameters (i.e. heart rate variability parameters) 206 indicative of patient activity. Additional IEGM data 208 also received from the pacing/sensing leads is used to derive respiration (i.e. breathing) related parameters 210 for analysis of sleep efficiency. A trans-thoracic impedance signal 212 detected between an implanted electrode and the housing of the device case is also used to generate the respiration related parameters 210.

The respiration related parameters are analyzed to detect IEGM-related changes indicative of IGT and/or glucose levels 214. Glucose levels may be derived from the IEGM using a variety of techniques then used to confirm any IGT or diabetes mellitus diagnosis. Blood glucose levels may be detected using the technique of the Kroll et al. patent application cited above (U.S. Patent Application 2004/0077962). See also techniques discussed in U.S. patent application Ser. No. 11/127,370, of Bharmi, filed May 11, 2005, entitled "System And Method For Distinguishing Between Hypoglycemia And Hyperglycemia Using An Implantable Medical Device" and U.S. patent application Ser. No. 11/117,624, also of Bharmi, filed Apr. 28, 2005, entitled "System and Method for Detecting Hypoglycemia Based on a Paced Depolarization Integral Using an Implantable Medical Device."

An implantable pressure sensor 216 (or other pressure sensing technique) is analyzed to extract blood pressure dynamics information (i.e. steady state and diurnal changes) 218. The activity sensor data 202, R-R interval data 206, IEGM-related data 214 and blood pressure data 218 are collectively analyzed by a diagnostics component 220, which may be the microcontroller of the pacer/ICD. The diagnostics generates warnings 222 as well as diagnostic information relevant to the direction of therapy 224 for review by the physician.

What have been described are various techniques for evaluating the likelihood of IGT and diabetes mellitus within a patient based on sleep quality and for assessing associated mortality risk. For the sake of completeness, a detailed description of an exemplary pacer/ICD for performing these functions will now be provided. However, principles of invention may be implemented within other implantable devices or within external devices based on data received from the implantable device.

Exemplary Pacer/ICD

FIG. 8 provides a simplified block diagram of the pacer/ICD of FIG. 1, which is a dual-chamber stimulation device capable of treating both fast and slow arrhythmias with stimulation therapy, including cardioversion, defibrillation, and pacing stimulation, as well as capable of evaluating the sleep quality of the patient and evaluating IGT, diabetes mellitus and associated mortality based on sleep quality. To provide atrial chamber pacing stimulation and sensing, pacer/ICD 10 is shown in electrical communication with a heart 312 by way of a right atrial lead 320 having a right atrial (RA) tip electrode 322 and an RA atrial ring electrode 323 implanted in the atrial appendage. Pacer/ICD 10 is also in electrical communication with the heart by way of a right ventricular lead 330 having, in this embodiment, a ventricular tip electrode 332, a right ventricular ring electrode 334, a right ventricular (RV) coil electrode 336, and a superior vena cava (SVC) coil electrode 338. Typically, the right ventricular lead 330 is transvenously inserted into the heart so as to place the RV coil electrode 336 in the right ventricular apex, and the SVC coil electrode 338 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 324 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 324 is designed to receive atrial and ventricular cardiac signals and to deliver left ventricular pacing therapy using at least a left ventricular tip electrode 326, left atrial pacing therapy using at least a left atrial ring electrode 327, and shocking therapy using at least a left atrial coil electrode 328. With this configuration, biventricular pacing can be performed. Although only three leads are shown in FIG. 8, it should also be understood that additional stimulation leads (with one or more pacing, sensing and/or shocking electrodes) may be used in order to efficiently and effectively provide pacing stimulation to the left side of the heart or atrial cardioversion and/or defibrillation.

Figure 9:
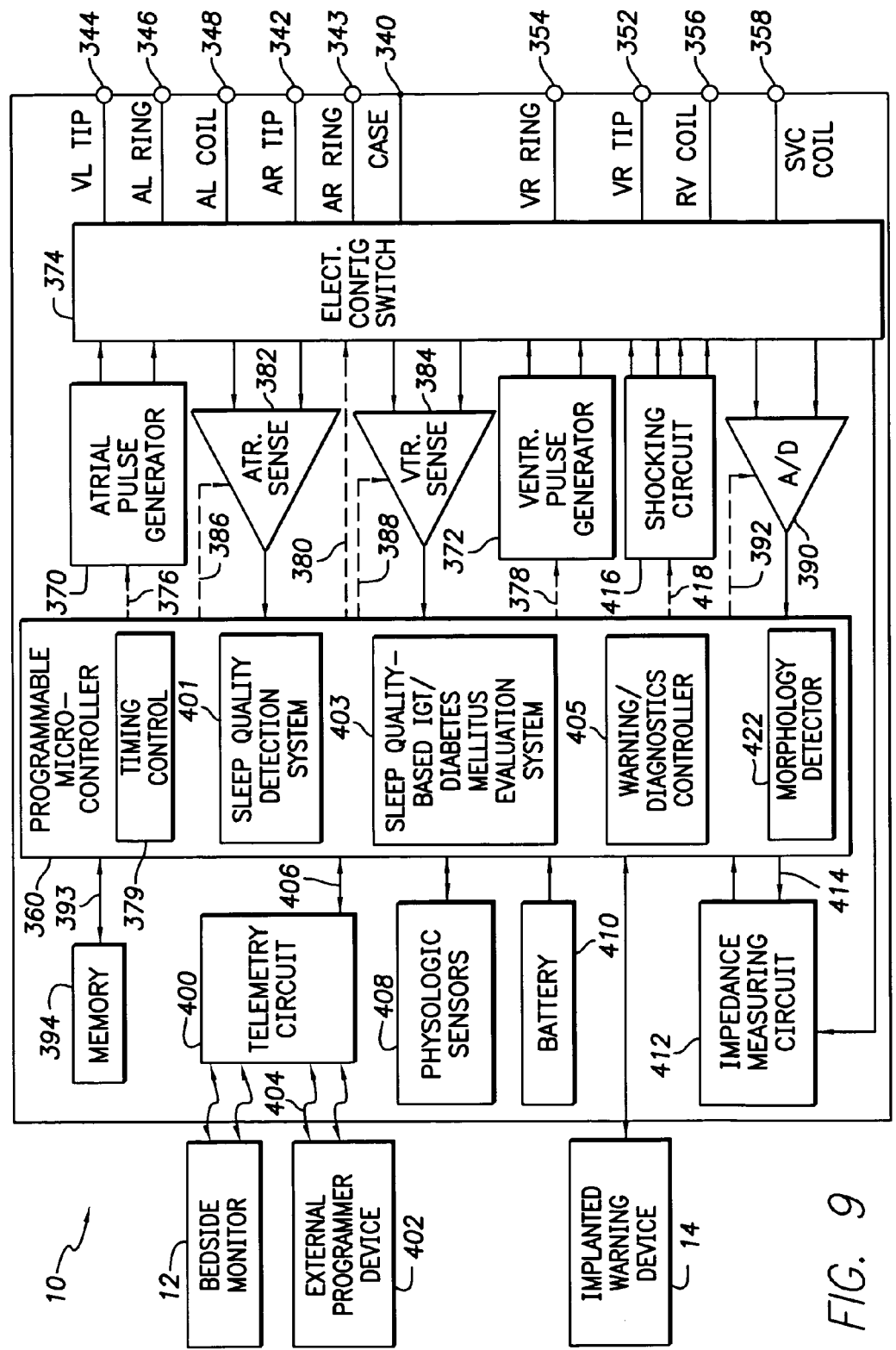
FIG. 9 is a functional block diagram of the pacer/ICD of FIG. 8, illustrating basic circuit elements that provide cardioversion, defibrillation and/or pacing stimulation in four chambers of the heart and particularly illustrating components for evaluating the likelihood that the patient has IGT or diabetes mellitus.

A simplified block diagram of internal components of pacer/ICD 10 is shown in FIG. 9. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy. The housing 340 for pacer/ICD 10, shown schematically in FIG. 9, is often referred to as the "can", "case" or "case electrode" and may be programmably selected to act as the return electrode for all "unipolar" modes. The housing 340 may further be used as a return electrode alone or in combination with one or more of the coil electrodes, 328, 336 and 338, for shocking purposes. The housing 340 further includes a connector (not shown) having a plurality of terminals, 342, 343, 344, 346, 348, 352, 354, 356 and 358 (shown schematically and, for convenience, the names of the electrodes to which they are connected are shown next to the terminals). As such, to achieve right atrial sensing and pacing, the connector includes at least a right atrial tip terminal ($A_R$ TIP) 342 adapted for connection to the atrial tip electrode 322 and a right atrial ring ($A_R$ RING) electrode 343 adapted for connection to right atrial ring electrode 323. To achieve left chamber sensing, pacing and shocking, the connector includes at least a left ventricular tip terminal ($V_L$ TIP) 344, a left atrial ring terminal ($A_L$ RING) 346, and a left atrial shocking terminal ($A_L$ COIL) 348, which are adapted for connection to the left ventricular ring electrode 326, the left atrial tip electrode 327, and the left atrial coil electrode 328, respectively. To support right chamber sensing, pacing and shocking, the connector further includes a right ventricular tip terminal ($V_R$ TIP) 352, a right ventricular ring terminal ($V_R$ RING) 354, a right ventricular shocking terminal ($R_V$ COIL) 356, and an SVC shocking terminal (SVC COIL) 358, which are adapted for connection to the right ventricular tip electrode 332, right ventricular ring electrode 334, the RV coil electrode 336, and the SVC coil electrode 338, respectively.

At the core of pacer/ICD 10 is a programmable microcontroller 360, which controls the various modes of stimulation therapy. As is well known in the art, the microcontroller 360 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 360 includes the ability to process or monitor input signals (data) as controlled by a program code stored in a designated block of memory. The details of the design and operation of the microcontroller 360 are not critical to the invention. Rather, any suitable microcontroller 360 may be used that carries out the functions described herein. The use of microprocessor-based control circuits for performing timing and data analysis functions are well known in the art.

As shown in FIG. 9, an atrial pulse generator 370 and a ventricular/impedance pulse generator 372 generate pacing stimulation pulses for delivery by the right atrial lead 320, the right ventricular lead 330, and/or the coronary sinus lead 324 via an electrode configuration switch 374. It is understood that in order to provide stimulation therapy in each of the four chambers of the heart, the atrial and ventricular pulse generators, 370 and 372, may include dedicated, independent pulse generators, multiplexed pulse generators or shared pulse generators. The pulse generators, 370 and 372, are controlled by the microcontroller 360 via appropriate control signals, 376 and 378, respectively, to trigger or inhibit the stimulation pulses. The microcontroller 360 further includes timing control circuitry 379 used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 374 includes a plurality of switches for connecting the desired electrodes to the appropriate I/O circuits, thereby providing complete electrode programmability. Accordingly, the switch 374, in response to a control signal 380 from the microcontroller 360, determines the polarity of the stimulation pulses (e.g., unipolar, bipolar, combipolar, etc.) by selectively closing the appropriate combination of switches (not shown) as is known in the art.

Atrial sensing circuits 382 and ventricular sensing circuits 384 may also be selectively coupled to the right atrial lead 320, coronary sinus lead 324, and the right ventricular lead 330, through the switch 374 for detecting the presence of cardiac activity in each of the four chambers of the heart. Accordingly, the atrial (ATR. SENSE) and ventricular (VTR. SENSE) sensing circuits, 382 and 384, may include dedicated sense amplifiers, multiplexed amplifiers or shared amplifiers. The switch 374 determines the "sensing polarity" of the cardiac signal by selectively closing the appropriate switches, as is also known in the art. In this way, the clinician may program the sensing polarity independent of the stimulation polarity. Each sensing circuit, 382 and 384, preferably employs one or more low power, precision amplifiers with programmable gain and/or automatic gain control, bandpass filtering, and a threshold detection circuit, as known in the art, to selectively sense the cardiac signal of interest. The automatic gain control, if provided, enables pacer/ICD 10 to deal effectively with the difficult problem of sensing the low amplitude signal characteristics of atrial or ventricular fibrillation. The outputs of the atrial and ventricular sensing circuits, 382 and 384, are connected to the microcontroller 360 which, in turn, are able to trigger or inhibit the atrial and ventricular pulse generators, 370 and 372, respectively, in a demand fashion in response to the absence or presence of cardiac activity in the appropriate chambers of the heart.

For arrhythmia detection, pacer/ICD 10 utilizes the atrial and ventricular sensing circuits, 382 and 384, to sense cardiac signals to determine whether a rhythm is physiologic or pathologic. As used in this section, "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 360 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 390. The data acquisition system 390 is configured to acquire intracardiac electrogram signals, convert the raw analog data into a digital signal, and store the digital signals for later processing and/or telemetric transmission to an external device 402. The data acquisition system 390 is coupled to the right atrial lead 320, the coronary sinus lead 324, and the right ventricular lead 330 through the switch 374 to sample cardiac signals across any pair of desired electrodes. The microcontroller 360 is further coupled to a memory 394 by a suitable data/address bus 396, wherein the programmable operating parameters used by the microcontroller 360 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

In addition, the stimulation device may be configured to perform Automatic Mode Switching (AMS) wherein the pacemaker reverts from a tracking mode such as a VDD or DDD mode to a nontracking mode such as VVI or DDI mode. VDD, DDD, VVI and DDI are standard device codes that identify the mode of operation of the device. DDD indicates a device that senses and paces in both the atria and the ventricles and is capable of both triggering and inhibiting functions based upon events sensed in the atria and the ventricles. VDD indicates a device that sensed in both the atria and ventricles but only paces in the ventricles. A sensed event on the atrial channel triggers ventricular outputs after a programmable delay, the pacemaker's equivalent of a PR interval. VVI indicates that the device is capable of pacing and sensing only in the ventricles and is only capable of inhibiting the functions based upon events sensed in the ventricles. DDI is identical to DDD except that the device is only capable of inhibiting functions based upon sensed events, rather than triggering functions. As such, the DDI mode is a non-tracking mode precluding its triggering ventricular outputs in response to sensed atrial events. Numerous other device modes of operation are possible, each represented by standard abbreviations of this type.

Advantageously, the operating parameters of the implantable pacer/ICD 10 may be non-invasively programmed into the memory 394 through a telemetry circuit 400 in telemetric communication with the external device 402, such as a programmer, transtelephonic transceiver or a diagnostic system analyzer. The telemetry circuit 400 is activated by the microcontroller by a control signal 406. The telemetry circuit 400 advantageously allows intracardiac electrograms and status information relating to the operation of pacer/ICD 10 (as contained in the microcontroller 360 or memory 394) to be sent to the external device 402 through an established communication link 404. Preferably, the telemetry circuit is also capable of relaying signals to a bedside monitor 12 (FIG. 1.)

Pacer/ICD 10 further includes an accelerometer or other physiologic sensor 408, commonly referred to as a "rate-responsive" sensor because it is typically used to adjust pacing stimulation rate according to the exercise state of the patient. Accordingly, the microcontroller 360 responds by adjusting the various pacing parameters (such as rate, AV Delay, V-V Delay, etc.) at which the atrial and ventricular pulse generators, 370 and 372, generate stimulation pulses. While shown as being included within pacer/ICD 10, it is to be understood that the physiologic sensor 408 may also be external to pacer/ICD 10, yet still be implanted within or carried by the patient. A common type of rate responsive sensor is an activity sensor incorporating an accelerometer or a piezoelectric crystal, which is mounted within the housing 340 of pacer/ICD 10. Other types of physiologic sensors are also known, for example, sensors that sense the oxygen content of blood, respiration rate and/or minute ventilation, pH of blood, ventricular gradient, etc. Block 408 is intended to represent any and all of the sensors discussed above in connection with the evaluation of sleep quality.

The pacer/ICD additionally includes a battery 410, which provides operating power to all of the circuits shown in FIG. 9. The battery 410 may vary depending on the capabilities of pacer/ICD 10. If the system only provides low voltage therapy, a lithium iodine or lithium copper fluoride cell may be utilized. For pacer/ICD 10, which employs shocking therapy, the battery 410 must be capable of operating at low current drains for long periods, and then be capable of providing high-current pulses (for capacitor charging) when the patient requires a shock pulse. The battery 410 must also have a predictable discharge characteristic so that elective replacement time can be detected. Accordingly, pacer/ICD 10 is preferably capable of high voltage therapy and appropriate batteries.

As further shown in FIG. 9, pacer/ICD 10 is shown as having an impedance measuring circuit 412 which is enabled by the microcontroller 360 via a control signal 414. Herein, impedance is primarily detected for use in detecting respiration. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used.

If pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 360 further controls a shocking circuit 416 by way of a control signal 418. The shocking circuit 416 generates shocking pulses of low (up to 0.5 joules), moderate (0.5-10 joules) or high energy (11 to 40 joules), as controlled by the microcontroller 360. Such shocking pulses are applied to the heart of the patient through at least two shocking electrodes, and as shown in this embodiment, selected from the left atrial coil electrode 328, the RV coil electrode 336, and/or the SVC coil electrode 338. The housing 340 may act as an active electrode in combination with the RV electrode 336, or as part of a split electrical vector using the SVC coil electrode 338 or the left atrial coil electrode 328 (i.e., using the RV electrode as a common electrode). Cardioversion shocks are generally considered to be of low to moderate energy level and pertain to the treatment of tachycardia. Defibrillation shocks are generally of moderate to high energy level (i.e., corresponding to thresholds in the range of 5-40 joules), are delivered asynchronously (since R-waves may be too disorganized), and pertain exclusively to the treatment of fibrillation. Accordingly, the microcontroller 360 is capable of controlling the synchronous or asynchronous delivery of the shocking pulses.

Microcontroller 360 also includes various components directed to evaluating IGT, diabetes mellitus and associated mortality based on sleep quality. In particular, a sleep quality detection system 401 operates to evaluate sleep quality using the techniques discussed above, particularly with reference to FIGS. 2-5. A sleep quality-based IGT/diabetes mellitus evaluation system 403 operates to evaluate the likelihood of the presence of IGT or diabetes mellitus with the patient and to assess associated mortality risk, using the techniques discussed above particularly with reference to FIG. 6. Warnings and/or diagnostic data are generated and controlled by warning/diagnostics controller 405. Warnings may be delivered via implanted warning device 14 and/or relayed to bedside monitor 12. Connection terminals for coupling the pacer/ICD to an implanted warning device are not separately shown. Instead, for clarity and simplicity, the warning device is shown as being functionally connected directly to the microcontroller. Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller.

Principles of the invention may be exploiting using other implantable devices or in accordance with other techniques. Indeed, general principles of the invention may be exploited with systems not incorporating pacemakers or ICDs but instead utilizing other implantable medical devices. As can be appreciated, a wide variety of specific implementations may be developed consistent with the principles of the invention and no attempt is made herein to describe or enumerate all such possible implementations. Thus, while the invention has been described with reference to particular embodiments, modifications can be made thereto without departing from the scope of the invention. Note also that the term "including" as used herein is intended to be inclusive, i.e. "including but not limited to."

What is claimed is:

1. A method for use with an implantable medical device for use within a patient, the method comprising:
   detecting a value representative of sleep quality of the patient; and
   evaluating the likelihood that the patient has an abnormal glucose level medical condition, the evaluation performed based on the sleep quality value.

2. The method of claim 1 wherein the abnormal glucose level medical condition includes one or more of impaired glucose intolerance (IGT) and diabetes mellitus.

3. The method of claim 1 wherein detecting sleep quality within the patient includes detecting sleep efficiency (SE) associated with a period of sleep.

4. The method of claim 3 wherein detecting sleep efficiency (SE) includes
   detecting a total quality sleep time (TQST) associated with a period of sleep;
   detecting a total amount of time the patient spent in the sleep position (TSSP) during the period of sleep; and
   calculating a ratio of total quality sleep time (TQST) to time spent in sleep position (TSSP).

5. The method of claim 4 wherein detecting total quality sleep time (TQST) includes:

detecting the onset (SO) of the period of sleep;
    detecting a final awakening (FA) from the period of sleep;
    calculating the total sleep period (TSP) as the time from sleep onset (SO) to final awakening (FA);
    detecting any time the patient spends moving (TSM) during the total sleep period (TSP);
    detecting any temporary awake time (TAT) during the total sleep period (TSP); and
    calculating total quality sleep time (TQST) as total sleep period (TSP) less any intervening time the patient spends moving (TSM) during the total sleep period (TSP) and less any temporary awake time (TAT) during the total sleep period (TSP).

6. The method of claim 5 wherein detecting sleep onset (SO) and detecting final awakening (FA) is performed, in part, based on changes in one or more of (a) heart rate variability, (b) cardiac signal morphology, (c) respiration rate and (d) respiration depth, each derived from an intracardiac electrogram (IEGM) of the patient sensed using implanted leads, and (e) blood pressure sensed using an implanted blood pressure sensor.

7. The method of claim 5 wherein detecting any time the patient spends moving (TSM) is performed, in part, based on changes in one or more of (a) the morphology of an IEGM of the patient sensed using implanted leads, (b) paced depolarization integral (PDI) sensed using implanted leads, and (c) patient movement sensed using an implanted activity sensor.

8. The method of claim 5 wherein detecting any temporary awake time (TAT) is performed, in part, based on changes in one or more of (a) heart rate variability derived from an IEGM sensed using implanted leads, (b) patient motion sensed using an implanted activity sensor and (c) blood pressure sensed using an implanted blood pressure sensor.

9. The method of claim 5 wherein detecting total time of the patient spent in sleep position (TSSP) is performed, in part, based on patient posture sensed using an implanted posture sensor.

10. The method of claim 1 wherein detecting sleep quality within the patient includes
    detecting a total sleep period (TSP); and
    determining an amount of deviation from a predetermined normal sleep range (NSR).

11. The method of claim 1 wherein evaluating the likelihood of that patient has the abnormal glucose level medical condition includes equating a decrease in sleep quality with an increased likelihood that the medical condition is present within the patient.

12. The method of claim 1 further including detecting an increased risk of mortality based on the sleep quality value.

13. The method of claim 12 wherein detecting an increased risk of mortality includes associating a decrease in sleep quality with an increased risk of mortality.

14. A system for use in an implantable medical device for use within a patient comprising:
    a sleep quality detection system operative to detect a value representative of sleep quality of the patient; and
    a sleep quality-based medical condition evaluation system operative to evaluate the likelihood that the patient has an abnormal glucose level medical condition, the evaluation performed based on the sleep quality value.

15. The system of claim 14 wherein the sleep quality detection system is operative to detect sleep efficiency (SE) associated with a period of sleep.

16. A system for use with an implantable medical device comprising:
    means for detecting a value representative of sleep quality of a patient in which the device is implanted;
    means for detecting an increased likelihood that the patient has an abnormal glucose level medical condition, the detection performed based on the sleep quality value; and
    means for controlling recordation of diagnostic information in response to the detection of an increased likelihood of the abnormal glucose level medical condition.

* * * * *